United States Patent [19]
Jezek

[11] Patent Number: 6,021,681
[45] Date of Patent: Feb. 8, 2000

[54] SAMPLING DEVICE WITH A CAPPED BODY AND DETACHABLE HANDLE

[75] Inventor: Gerd-Rainer Jezek, Orchard Park, N.Y.

[73] Assignee: The United States of America as represented by the United States Department of Energy, Washington, D.C.

[21] Appl. No.: 08/884,350

[22] Filed: Jun. 27, 1997

[51] Int. Cl.[7] .................................................. G01N 1/04

[52] U.S. Cl. ............................................. 73/864.71

[58] Field of Search ..................... 600/576, 580, 600/584; 73/864.71, 864.72; 435/30, 309.1

[56] References Cited

U.S. PATENT DOCUMENTS

| | | | |
|---|---|---|---|
| 2,835,246 | 5/1958 | Boettger | 73/864.71 |
| 3,368,549 | 2/1968 | Barr et al. | 435/309.1 |
| 3,783,106 | 1/1974 | Henshilwood | 435/30 |
| 4,803,998 | 2/1989 | Kezes et al. | 435/309.1 |
| 5,078,968 | 1/1992 | Nason | 435/309.01 |
| 5,163,441 | 11/1992 | Monthony et al. | 435/30 |

*Primary Examiner*—Robert Raevis
*Attorney, Agent, or Firm*—Joy A. Alwan; Thomas G. Anderson; William R. Moser

[57] ABSTRACT

The apparatus is a sampling device having a pad for sample collection, a body which supports the pad, a detachable handle connected to the body and a cap which encloses and retains the pad and body to protect the integrity of the sample.

14 Claims, 2 Drawing Sheets

SAMPLING DEVICE WITH A CAPPED BODY AND DETACHABLE HANDLE

CONTRACTUAL ORIGINS OF THE INVENTION

The United States government has rights in this invention pursuant to contract number DE-AC07-81NE44139 between the United States Department of Energy and West Valley Nuclear Services.

BACKGROUND OF THE INVENTION

The present invention relates to a device for sampling radioactive waste and more particularly to a device for sampling radioactive waste which prevents contamination of a sampled material and the environment surrounding the sampled material.

During vitrification of nuclear wastes, it is necessary to remove contamination from the surfaces of canisters filled with radioactive glass. After removal of contamination, a sampling device is used to test the surface of the canister. The one piece sampling device currently in use creates a potential for spreading contamination during vitrification operations. During operations, the one piece sampling device is transferred into and out of the vitrification cell through a transfer drawer. Inside the cell, a remote control device handles the sampling device to wipe the surface of the canister. A one piece sampling device can be contaminated by the remote control device prior to use. Further the sample device can also contaminate the transfer drawer producing false readings for radioactive material. The present invention overcomes this problem by enclosing the sampling pad in a cap. The removable handle is reused which reduces the amount of waste material.

SUMMARY OF THE INVENTION

It is an objective of the present invention to provide an enclosed sampling device which protects the sample from contamination. A feature of the present invention is a cap to enclose and protect the sample.

It is a further objective of the invention to prevent the sample from contaminating the surrounding environment. In addition to the cap enclosing the sample, a feature of the present invention is a means to detach the handle from the sampling device before the sample is removed from the cell.

It is a further objective of the invention to provide a tamper proof container for the sample.

It is a further objective of the invention to provide a sampling device which can be operated by remote control.

In brief, the above objectives and advantages of the invention are met by a sampling device comprising a pad for collecting samples, a body supporting the pad, a detachable handle, and a cap that encloses and protects the sample.

Additional objects, advantages and novel features of the invention will be set forth in part in the description which follows, and in part will become apparent to those skilled in the art upon examination of the following or may be learned by practice of the invention. The objects and advantages of the invention may be realized and obtained by means of the instrumentalities and combinations particularly pointed out in the appended claims.

DETAILED DESCRIPTION OF THE INVENTION

Figure 1:
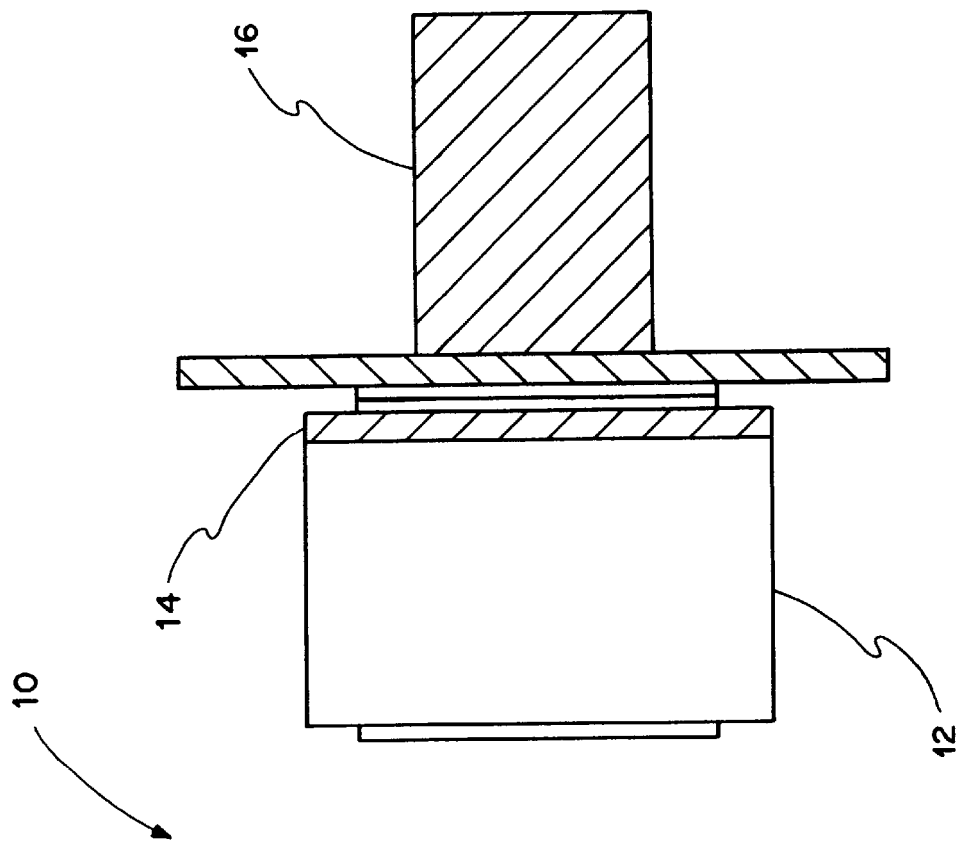
FIG. 1 is a side plan view of the sampling device in accordance with the features of this invention.
Figure 1:
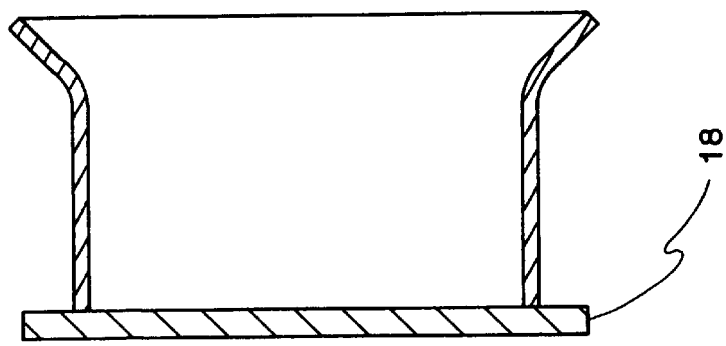

Referring to FIG. 1, a plan side view of the sampling device is shown 10. A sample is collected on a sorbent pad 12. The pad can be composed of any sterile or uncontaminated sorbent material. The pad as shown in FIG. 1 is a polychlorinated organic material. Materials such as natural sponge, surgical sponge or fiber gauze could also be used. For certain applications a thin pad of sterile woven material may be attached to the end of the sponge which is in contact with the material to be sampled. Alternatively the pad may be composed of a sterile, adhesive material. The pad 12 is attached to a rigid body 14. The body in turn is attached to a handle 16. In the preferred embodiment the body and handle are attached by a pair of hook and loop fasteners. One of the pair is attached to the body and the other is attached to the handle so that the handle may be separated from the body. After the sample is collected the pad 12 and body 14 are enclosed in a cap 18. The cap is designed to totally enclose and retain the pad and body of the sampling device.

In the preferred embodiment, the pad is slightly larger in diameter than the interior of the cap so that the cap is retained by the expansion of the pad. In other embodiments, the cap and body are threaded to screw the body into the cap. The body and cap may be designed to cross thread, preventing the body from being removed from the cap once the parts a threadedly joined.

Figure 2:
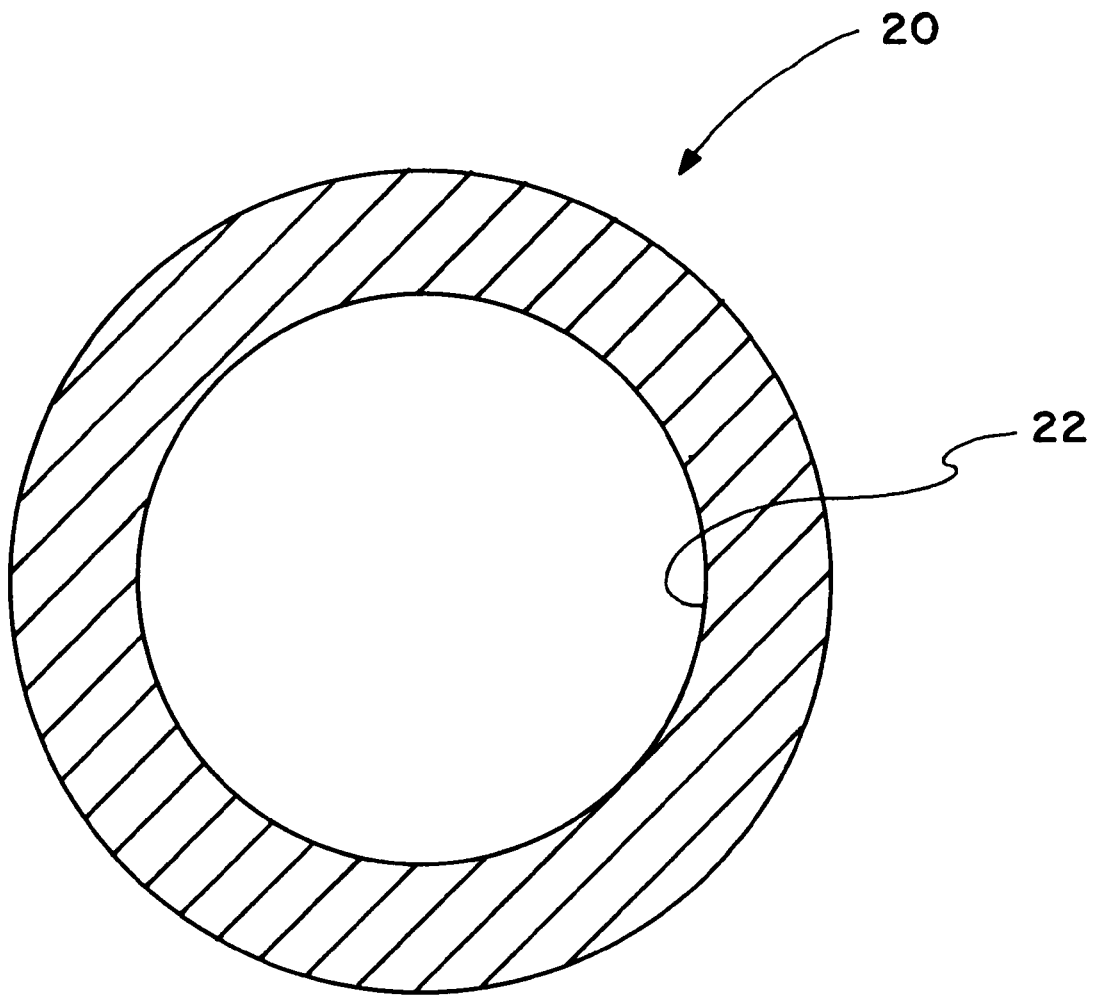
FIG. 2 is a cross sectional view of the device for cutting the handle from the body of the sampling device.

FIG. 2 shows the means for separating the handle from the body. In the preferred embodiment of the invention, a cutting ring 20 is a hollow tube with open ends. The interior diameter of the cutting ring has a diameter greater than the cap of the sampling device. In the preferred embodiment the tube is composed of stainless steel but may be comprised of any suitable rigid material. One end of the tube is attached to a transfer drawer 28. The other end has a circular opening smaller than the circumference of the tube with a sharp interior cutting edge. The circular cutting edge serves to separate the capped sampling device from the handle.

In the preferred embodiment operation the sampling device is inserted in a transfer drawer and transferred into a vitrification cell. A remote control device 30 inserts the sampling device into a grooved cap holder 24 attached to the transfer drawer for removing the cap 18 and exposing the pad 12. The pad is then wiped on the material to be sampled. The cap is then replaced to eliminate contamination. The capped sampling device is then inserted into the cutting ring 20 and force is applied to separate the cap and body from the handle. The enclosed sample drops through the hollow tube into the transfer drawer and is removed from the cell. The handle is reused.

While the invention has been described with reference to details of the illustrated embodiment, these details are not intended to limit the scope of the invention as defined in the appended claims.

The embodiment of the invention in which an exclusive property or privilege is claimed is defined as follows:

1. A sampling device comprising:

a pad for collecting samples;

a body attached to the pad where the body provides support for the pad;

a detachable handle connected to the body;

a means for detaching the handle; and a cap which encloses and retains the pad and body to protect the integrity of the sample.

2. The sampling device of claim 1 wherein the pad is composed of sterile material.

3. The sampling device of claim 1 wherein the pad is composed of a sorbent material.

4. The sampling device of claim 1 wherein the pad is composed of a adhesive material.

5. The sampling device of claim 1, wherein the device has a means for remote operation.

6. The sampling device of claim 1, wherein the means for detaching the handle is a cutting ring comprising a hollow tube having an interior cutting edge on an end of the tube.

7. The sampling device of claim 1, wherein the detachable handle is connected to the body by a hook and loop strips of interlocking material.

8. The sampling device of claim 1 wherein the cap is threadedly attached to the body.

9. The sampling device of claim 1 wherein the cap, body and handle are composed of a plastic material.

10. A sampling device comprising:

a sterile pad for collecting samples;

a body attached to the pad where the body provides support for the pad;

a detachable handle connected to the body;

a hollow tube having an interior cutting edge on an end of the tube for detaching the handle from the body;

a cap which encloses the pad and body to protect the integrity of the sample, said cap and body being threadedly connected; and a cap holder to securely hold the cap while the sterile pad, body and handle are in use.

11. The sampling device of claim 10 wherein the pad is composed of a sorbent material.

12. The sampling device of claim 10 wherein the pad is composed of a adhesive material.

13. The sampling device of claim 10, wherein the cap holder is a grooved bracket which securely holds the cap.

14. The sampling device of claim 10 wherein the cap, body and handle are composed of a plastic material.

* * * * *